(12) United States Patent
Wang

(10) Patent No.: US 10,828,199 B2
(45) Date of Patent: Nov. 10, 2020

(54) GOGGLES

(71) Applicant: WENZHOU DONGYI OPTICS LIMITED, Wenzhou (CN)

(72) Inventor: Wenti Wang, Wenzhou (CN)

(73) Assignee: WENZHOU DONGYI OPTICS LIMITED, Wenzhou (CN)

( * ) Notice: Subject to any disclaimer, the term of this patent is extended or adjusted under 35 U.S.C. 154(b) by 378 days.

(21) Appl. No.: 15/778,229

(22) PCT Filed: Mar. 25, 2016

(86) PCT No.: PCT/CN2016/077310
§ 371 (c)(1),
(2) Date: May 23, 2018

(87) PCT Pub. No.: WO2017/117872
PCT Pub. Date: Jul. 13, 2017

(65) Prior Publication Data
US 2018/0338863 A1   Nov. 29, 2018

(30) Foreign Application Priority Data

Jan. 8, 2016   (CN) .......................... 2016 1 0011197

(51) Int. Cl.
*A61F 9/02*   (2006.01)

(52) U.S. Cl.
CPC .............. *A61F 9/028* (2013.01); *A61F 9/025* (2013.01); *A61F 9/026* (2013.01); *A61F 9/027* (2013.01)

(58) Field of Classification Search
CPC .......... A61F 9/028; A61F 9/025; A61F 9/026; A61F 9/027; A61F 9/02; G02C 11/08

USPC ............ 2/426, 430, 431, 435–437, 439, 447
See application file for complete search history.

(56) References Cited

U.S. PATENT DOCUMENTS

| | | | | |
|---|---|---|---|---|
| 1,900,955 | A * | 3/1933 | Shindel | A61F 9/028 2/437 |
| 2,877,463 | A * | 3/1959 | Watkins | A61F 9/028 2/437 |
| 3,081,461 | A * | 3/1963 | Gurtowski | A61F 9/026 2/441 |
| 3,141,172 | A * | 7/1964 | Hirschmann | A61F 9/028 2/436 |
| 3,418,658 | A * | 12/1968 | Danico | A62B 18/08 2/436 |
| 3,638,240 | A * | 2/1972 | Militello | A61F 9/028 2/437 |

(Continued)

FOREIGN PATENT DOCUMENTS

| | | |
|---|---|---|
| CN | 2481306 Y | 3/2002 |
| CN | 2652360 Y | 11/2004 |

(Continued)

*Primary Examiner* — Jameson D Collier
(74) *Attorney, Agent, or Firm* — Bayramoglu Law Offices LLC

(57) ABSTRACT

Goggles include a main frame of goggles, a lens, an exhaust valve and a nose pad supporter. The exhaust valves and the nose pad supporter are disposed on the main frame of goggles and are integrally molded with the main frame of goggles. The main frame of the goggles is wrapped outside the lens, and the lens is clamped in the main frame of goggles. The goggles can keep tight structure and have a good air permeability, and prevent blood and other liquids from spattering into the goggles.

7 Claims, 2 Drawing Sheets

(56) References Cited

U.S. PATENT DOCUMENTS

| | | | | |
|---|---|---|---|---|
| 4,027,342 A | * | 6/1977 | Hirschmann, Jr. | A61F 9/028 2/436 |
| 4,264,988 A | * | 5/1981 | Specht | A61F 9/028 2/431 |
| 4,435,852 A | | 3/1984 | Nesler | |
| 4,670,914 A | * | 6/1987 | Harris | A61F 9/028 2/426 |
| 4,977,627 A | * | 12/1990 | Metcalfe | A61F 9/028 2/437 |
| 5,452,480 A | * | 9/1995 | Ryden | A61F 9/028 2/171.3 |
| 5,652,965 A | | 8/1997 | Crooks | |
| 5,657,106 A | * | 8/1997 | Herald, Jr. | A61F 9/025 2/437 |
| 6,772,448 B1 | * | 8/2004 | Hockaday | A61F 9/028 2/435 |
| 2003/0033661 A1 | * | 2/2003 | Huh | A61F 9/028 2/436 |
| 2008/0276356 A1 | * | 11/2008 | Lee | A61F 9/028 2/436 |
| 2014/0259320 A1 | * | 9/2014 | Gonzalez | A61F 9/028 2/424 |

FOREIGN PATENT DOCUMENTS

| | | |
|---|---|---|
| CN | 2853028 Y | 1/2007 |
| CN | 201812100 U | 4/2011 |
| CN | 205359785 U | 7/2016 |

\* cited by examiner

GOGGLES

CROSS REFERENCE TO RELATED APPLICATIONS

This application is the national phase entry of International Application PCT/CN2016/077310, filed on Mar. 25, 2016, which is based upon and claims priority to Chinese Patent Application No. 201610011197.8, filed on Jan. 8, 2016, the entire contents of which are incorporated herein by reference.

TECHNICAL FIELD

The present invention relates to goggles suitable for laboratories, chemical plants, and hospitals, and particularly to goggles, where the components of the goggles can be integrally and tightly connected with each other when changing external conditions.

BACKGROUND

In order to prevent infections or other injuries caused by potions and patient's blood spattering on the doctor's face, doctors need to wear protective eyepatches, which can be used together with masks, surgical caps, etc. It provides comprehensive protection to the doctor's head. The traditional eyepatches for medical purposes has poor air permeability and can not fit the face well, and because of their hard material, these are not comfortable to use, and get easily deformed when the external conditions change.

During the experiments in the laboratory and the production in the chemical plant, eyepatches are required. Because the various components of the existing eyepatches are assembled, they get easily deformed with the change in external conditions. As a result, the components can not be tightly connected to each other, thus generating seam and causing the harmful liquid to flow into the eyepatch and causing harm to the human body.

During the long distance transportation, the external conditions change, resulting in the deformation of the components of the assembled goggles and the weakening the protective capability.

Chinese patent No. 03237806.8 discloses a protective eyepatch, including an eyepatch frame and a lens. The lens is inserted in a groove with a certain depth at the inner side of the front end of the eyepatch frame which can cover the eyes tightly close to the periphery of eyes. On both sides of the eyepatch frame, a buckle is provided to attach to a fixed belt. On the periphery of the eyepatch frame, through holes are provided and a waterproof and breathable device is inserted in the through hole edge. The eyepatch frame includes the main eyepatch frame and the middle nose frame, and the main eyepatch frame and the middle nose frame overlap at the protuberance of the lens. However, the eyepatch needs to be provided with an additional waterproof and breathable device at the through hole, which is clamped at the through hole by the groove, thereby weakening the overall mechanical strength of the eyepatch frame. Besides, the waterproof and breathable device is composed of breathable parts and waterproof parts, the manufacturing process is complex and the usage cost is increased. The waterproof and breathable device needs to be in one-to-one correspondance with the through hole, so it is inconvenient to use. The eyepatch frame composed of the main eyepatch frame and the middle nose frame reduces the mechanical strength. After a long time of use, the joint is prone to break or produce a seam, and the droplets may enter inside the eyepatch from the seam. The protective eyepatch needs to be immersed in potions, and can not be directly and repeatedly used by high temperature sterilization, which also increases the usage cost and shortens the service life.

SUMMARY

To solve the above-mentioned technical problems, the present invention provides goggles, in which the components of the goggle can be tightly connected with each other when changing external conditions.

The objectives of the present invention are realized by the following technical solutions.

Goggles includes a main frame of the goggles, a lens, exhaust valves and a nose pad supporter. The exhaust valves and nose pad supporter are disposed on the main frame of the goggles and are integrally molded with the main frame of the goggles. The main frame of the goggles is wrapped outside the lens, and the lens is clamped in the main frame of the goggles.

Further, the main frame of the goggles is strip-like. One end is provided with the nose pad supporter and the other end is provided with a male and female type connection device. The nose pad supporter is provided with a male and female type connection device matched with the male and female type connection device on the main frame of the goggles. The main frame of the goggles is wrapped outside the lens, which is fixed through the matched male and female type connection devices.

Further, the male and female type connection device on the main frame of the goggles is a buckle hole, and the male and female type connection device on the nose pad supporter is a buckle.

Further, the inner side of the main frame of the goggles is provided with clamping grooves. The periphery of the lens is clamped in the clamping groove and is surrounded by the clamping groove, so that the lens and the main frame of the goggles are kept sealed.

Further, the exhaust valves are disposed on the outer wall of the main frame of the goggles. The exhaust valves and the main frame of the goggles are molded integrally. The section of the exhaust valve is double bowl-shaped and inverted on the main frame of the goggles.

Further, the inner layer of the double bowl-shaped exhaust valve is provided with a vent hole which is connected to the inner side of the main frame of the goggles. The outer layer of the double bowl-shaped shaped exhaust valve covers the inner layer to form a ventilation passage between the inner layer and outer layer, and an extended ventilation passage is formed between the outer wall of the main frame of the goggles and the out layer.

Further, the outer wall of the main frame of the goggles is provided with two symmetrical connection buckles.

Further, the lens includes a left lens, a right lens and a nose pad. The left and right lenses and the nose pad are molded integrally.

Further, the exhaust valve is integrally molded into an hourglass shape, the wall of the upper exhaust valve turns downwards to cover the wall of lower exhaust valve to form a double bowl-shape.

Further, the main frame of the goggles is provided with a hole matched with the lens. The lens is inserted in the hole. A trumpet-shaped extending segment is formed between the end fixing the lens and the end tightly close to the face on the main frame of the goggles.

Advantages of the present invention are as follows.

First, the exhaust valve, the nose pad supporter and the main frame of the goggles are molded integrally. The goggles can be wholly and tightly connected with each other when changing external conditions. Second, the goggles has exhaust valves, which can form an airflow circulation in use. Therefore, it is convenient to wear and air permeability is better. Third, double exhaust valve effectively prevents blood and other liquids from spattering into the goggles. Fourth, labor cost can be saved, and assembly steps can be reduced, thus improving efficiency.

DETAILED DESCRIPTION

Hereinafter, the present invention will be described in detail through the embodiments with reference to the drawings.

Figure 1:
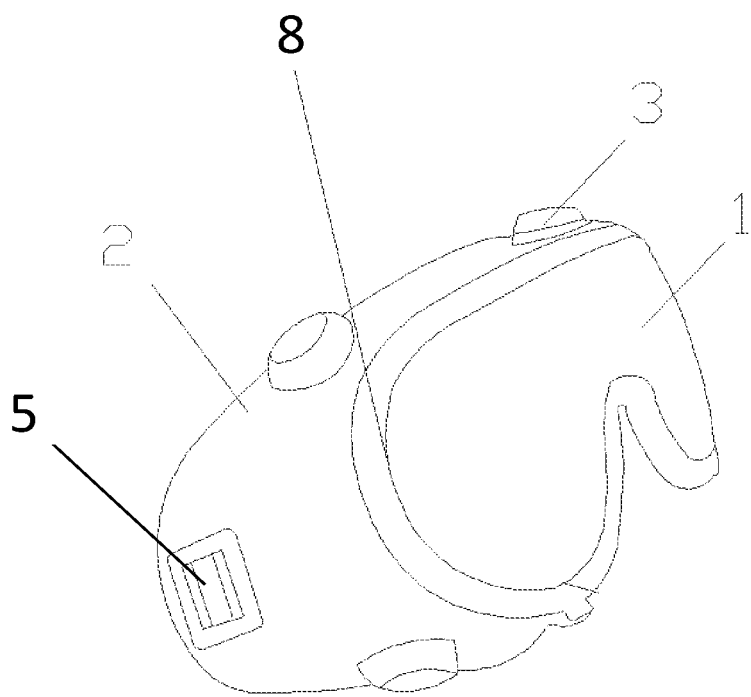
FIG. 1 is a schematic diagram of the present invention.
Figure 2:
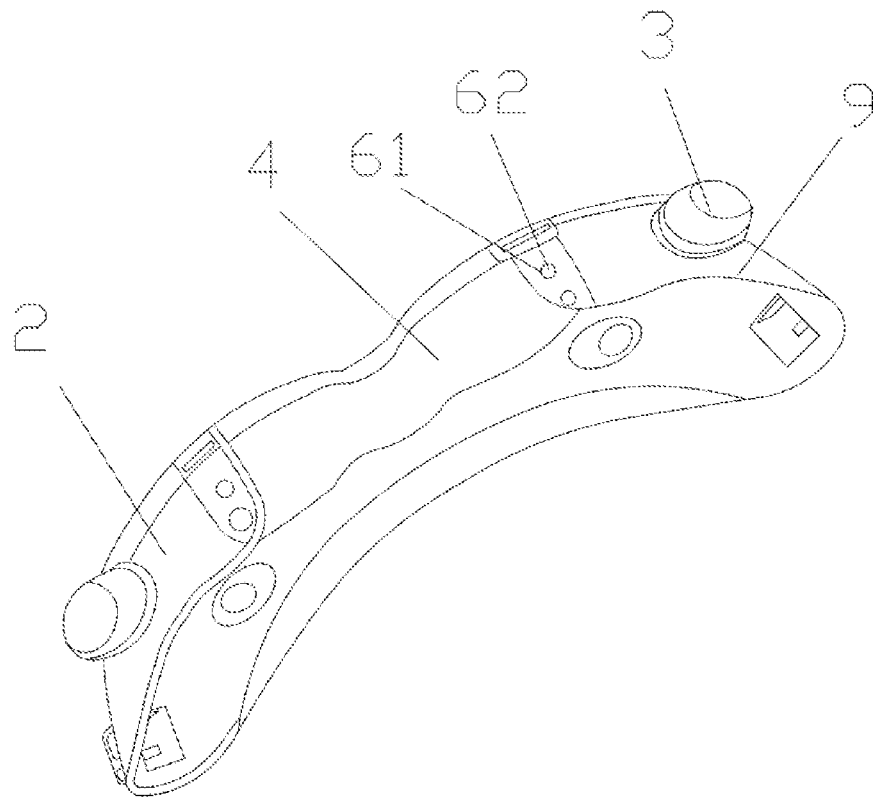
FIG. 2 is a perspective view of the present invention.
Figure 3:
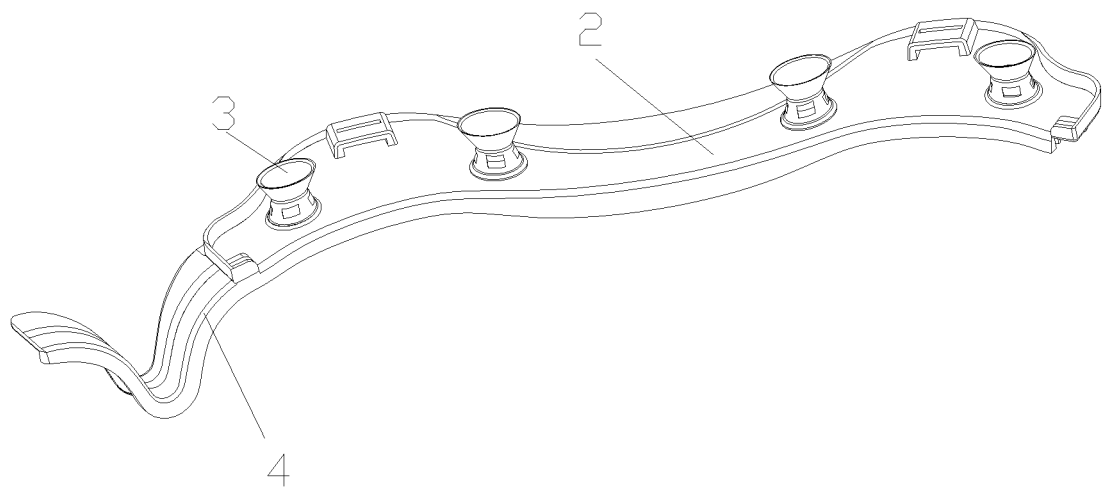
FIG. 3 is a schematic view of the main frame of the goggles.
Figure 4:
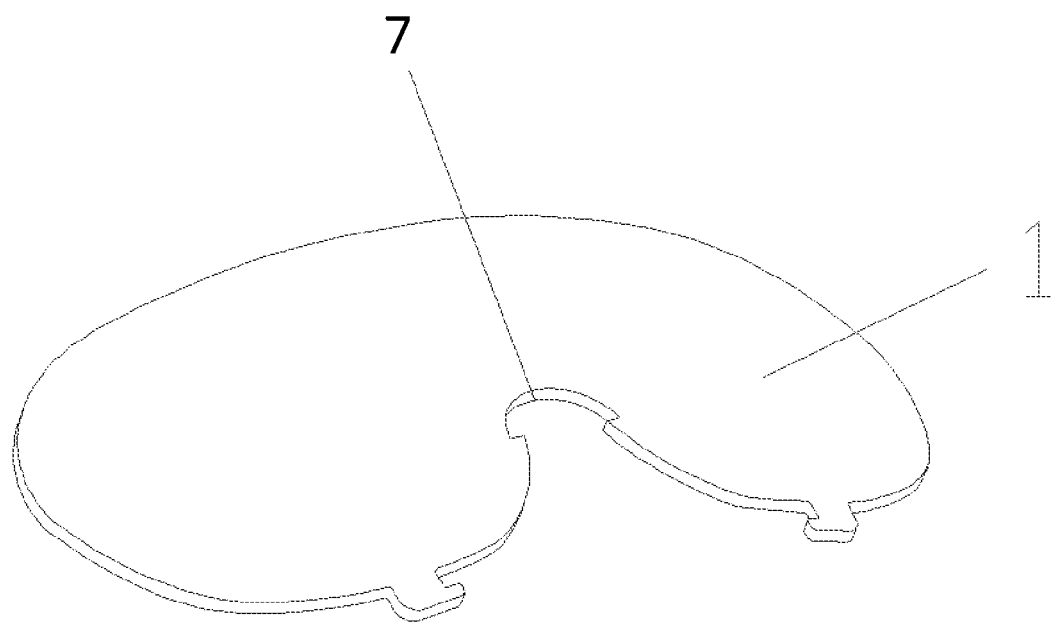
FIG. 4 is a schematic view of the lens.

As shown in FIGS. 1-4, goggles include a main frame of goggles 2, a lens 1, an exhaust valve 3 and a nose pad supporter 4. The exhaust valves 3 and the nose pad supporter 4 are disposed on the main frame of goggles 2 and are integrally molded with the main frame of goggles 2. The main frame of the goggles 2 is wrapped outside the lens 1, and the lens 1 is clamped in the main frame of goggles 2. The exhaust valves 3, the nose pad supporter 4 and the main frame of goggles 2 are integrally molded, when changing the external conditions, the goggles can be integrally and tightly connected to avoid other liquids spattering into the goggles.

The main frame of the goggles 2 is strip-like. One end is provided with a nose pad supporter 4 and the other end is provided with a male and female type connection device 61. The nose pad supporter 4 has a male and female type connection device 62 matched with the male and female type connection device 61 on the main frame of goggles 2. The main frame of goggles 2 is wrapped outside the lens 1, which is fixed through the matched male and female type connection devices.

One end of the nose pad supporter 4 and the main frame of goggles 2 are integrally molded. The other end is provided with a male and female type connection device 62.

The male and female type connection device 61 on the main frame of goggles 2 is a buckle hole, and the male and female type connection device 62 on the nose pad supporter 4 is a buckle.

The inner side of the main frame of goggles 2 has clamping grooves. The periphery of the lens 1 is clamped in the clamping groove and is surrounded by the clamping groove so that the lens 1 and the main frame of goggles 2 are kept sealed.

The exhaust valves are disposed on the outer wall of the main frame of goggles 2. The exhaust valves 3 and the main frame of goggles 2 are molded integrally. The section of the exhaust valve 3 is double bowl-shaped and inverted on the main frame of goggles 2.

The inner layer of the double bowl-shaped exhaust valve 3 has a vent hole which is connected to the inner side of the main frame of goggles 2. The outer layer of the double bowl-shaped shaped exhaust valve 3 covers the inner layer to form a ventilation passage between the inner layer and outer layer, and an extended ventilation passage is formed between the outer wall of the main frame of goggles 2 and the out layer.

The outer wall of the main frame of goggles is provided with two symmetrical connection buckles 5.

The lens 1 includes a left lens, a right lens and a nose pad 7. The left and right lenses and the nose pad 7 are molded integrally.

The nose pad 7 of the lens 1 is mushroom-like.

The exhaust valve 3 is integrally molded into an hourglass shape, the wall of the upper exhaust valve turns downwards to cover the wall of lower exhaust valve to form a double bowl-shaped.

The main frame of goggles 2 is provided with a hole 8 matched with the lens. The lens 1 is inserted in the hole 8. A trumpet-shaped extending segment 9 is formed between the end of fixing the lens 1 and the end tightly close to the face on the main frame of goggles 2.

The edge of the end tightly close to the face of the main frame of goggles 2 is provided with a soft joint surface, which is suitable for various face types.

The section of the edge of the end close to the face of the main frame of goggles 2 is splay. When the goggles are worn, the opening inner side of the spray edge is close to the face, which effectively prevents the liquid from entering into the goggles through the edge of the end close to the face in the main frame of goggles 2.

A mold for making a main frame of goggles, a cavity is formed inside the mold. The shape of the cavity is the same as the combination of the main frame of goggles, the exhaust valve 3 and the nose pad supporter 4. The shape of the exhaust valve is hourglass-like.

Although the present invention has been illustrated and described by referring to the preferred embodiment, the ordinary person skilled in the art should understand that it may not be limited to the description of the above embodiment and various changes in form and detail can be made within the scope of the claims.

What is claimed is:

1. Goggles, comprising:
   a main frame of the goggles,
   a lens, an exhaust valve, and
   a nose pad supporter; wherein
   the exhaust valve and the nose pad supporter are disposed on the main frame of the goggles, and the exhaust valve and the nose pad supporter are integrally molded with the main frame of the goggles;
   the main frame of the goggles is wrapped outside the lens, and the lens is clamped in the main frame of the goggles, wherein
   the exhaust valve is integrally molded into an hourglass-shaped exhaust valve;
   a wall of an upper exhaust valve portion of the exhaust valve turns downwards to cover a wall of a lower exhaust valve portion of the exhaust valve to form the exhaust valve.

2. The goggles of claim 1, wherein
   the main frame of the goggles is in a form of a strip;
   a first end of the main frame of the goggles is provided with the nose pad supporter, and a second end of the main frame of the goggles is provided with a first male and female type connection device;
   the nose pad supporter is provided with a second male and female type connection device, the second male and female type connection device is configured to be connected to the first male and female type connection device on the main frame of the goggles.

3. The goggles of claim 1, wherein
the exhaust valve is disposed on an outer wall of the main frame of the goggles;
a section of the hourglass-shaped exhaust valve is double bowl-shaped, and the exhaust valve is inverted on the main frame of the goggles.

4. The goggles of claim 1, wherein
the hourglass shape of the exhaust valve is a double bowl shape and the double bowl, hourglass-shaped exhaust valve has an inner layer, the inner layer is provided with a vent hole, the vent hole is connected to an inner side of the main frame of the goggles;
an outer layer of the double bowl, hourglass-shaped exhaust valve covers the inner layer of the double bowl, hourglass-shaped exhaust valve to form a ventilation passage between the inner layer of the double bowl, hourglass-shaped exhaust valve and the outer layer of the double bowl, hourglass-shaped exhaust valve, and an extended ventilation passage is formed between an outer wall of the main frame of the goggles and the outer layer of the double bowl, hourglass-shaped exhaust valve.

5. The goggles of claim 1, wherein
an outer wall of the main frame of the goggles is provided with two buckles.

6. The goggles of claim 1, wherein
the lens comprises a left lens pin, a right lens portion and a nose pad-portion;
the left lens portion, the right lens portion and the nose pad portion are molded integrally.

7. The goggles of claim 1, wherein
the main frame of the goggles is provided with a hole, the hole is matched with the lens;
the lens is inserted in the hole;
a first end of the main frame of the goggles is used to fix the lens, and a second end of the main frame of the goggles is configured to be close to a face.

* * * * *